United States Patent
Haberland

(10) Patent No.: US 8,161,802 B2
(45) Date of Patent: Apr. 24, 2012

(54) HANDHELD TENSIOMETER FEATURING AUTOMATIC REGULATION OF THE BUBBLE LIFE BY MEASURING AND REGULATING THE GAS VOLUME FLOW

(75) Inventor: Ralf Haberland, Dresden (DE)

(73) Assignee: Sita Messtechnik GmbH, Dresden (DE)

(*) Notice: Subject to any disclaimer, the term of this patent is extended or adjusted under 35 U.S.C. 154(b) by 678 days.

(21) Appl. No.: 12/224,416

(22) PCT Filed: Mar. 28, 2007

(86) PCT No.: PCT/DE2007/000564
§ 371 (c)(1),
(2), (4) Date: Aug. 25, 2008

(87) PCT Pub. No.: WO2007/115532
PCT Pub. Date: Oct. 18, 2007

(65) Prior Publication Data
US 2009/0133479 A1 May 28, 2009

(30) Foreign Application Priority Data
Apr. 4, 2006 (DE) .......................... 10 2006 017 152

(51) Int. Cl.
*G01N 13/02* (2006.01)
(52) U.S. Cl. ..................................... 73/64.48
(58) Field of Classification Search .............. 73/64.48, 73/64.51
See application file for complete search history.

(56) References Cited

U.S. PATENT DOCUMENTS

| | | | | |
|---|---|---|---|---|
| 6,185,989 | B1* | 2/2001 | Schulze | 73/64.51 |
| 7,481,097 | B2* | 1/2009 | Schumann et al. | 73/64.51 |
| 2007/0277597 | A1* | 12/2007 | Schumann et al. | 73/64.51 |

FOREIGN PATENT DOCUMENTS

| | | |
|---|---|---|
| DE | 28609646 | 3/1996 |
| DE | 19529787 | 2/1997 |
| DE | 19636644 | 7/1997 |
| DE | 20310173 | 9/2003 |
| DE | 20318463 | 3/2004 |
| DE | 202004012573 | 12/2004 |
| EP | 0760472 | 3/1997 |
| EP | 0902887 | 3/1999 |

OTHER PUBLICATIONS

Pocketdyne Sep. 2004—Kruss Technische Infromation.
Pocketdyne Feb. 2007—Kruss Technical Information "Bubble Pressure Tensiometer".

* cited by examiner

*Primary Examiner* — John Fitzgerald
(74) *Attorney, Agent, or Firm* — Horst M Kasper

(57) ABSTRACT

A hand tensiometer for measuring the surface tension of liquids or for measuring of substance concentrations in a liquid wherein a gas volume stream entered from a gas source (10) through a buffer storage (11) into a measuring capillary (3) forms bubbles in the liquid at the end of the measuring capillary (3), and wherein means for steady measuring and for adjusting the gas volume stream are furnished.

Figure 1:
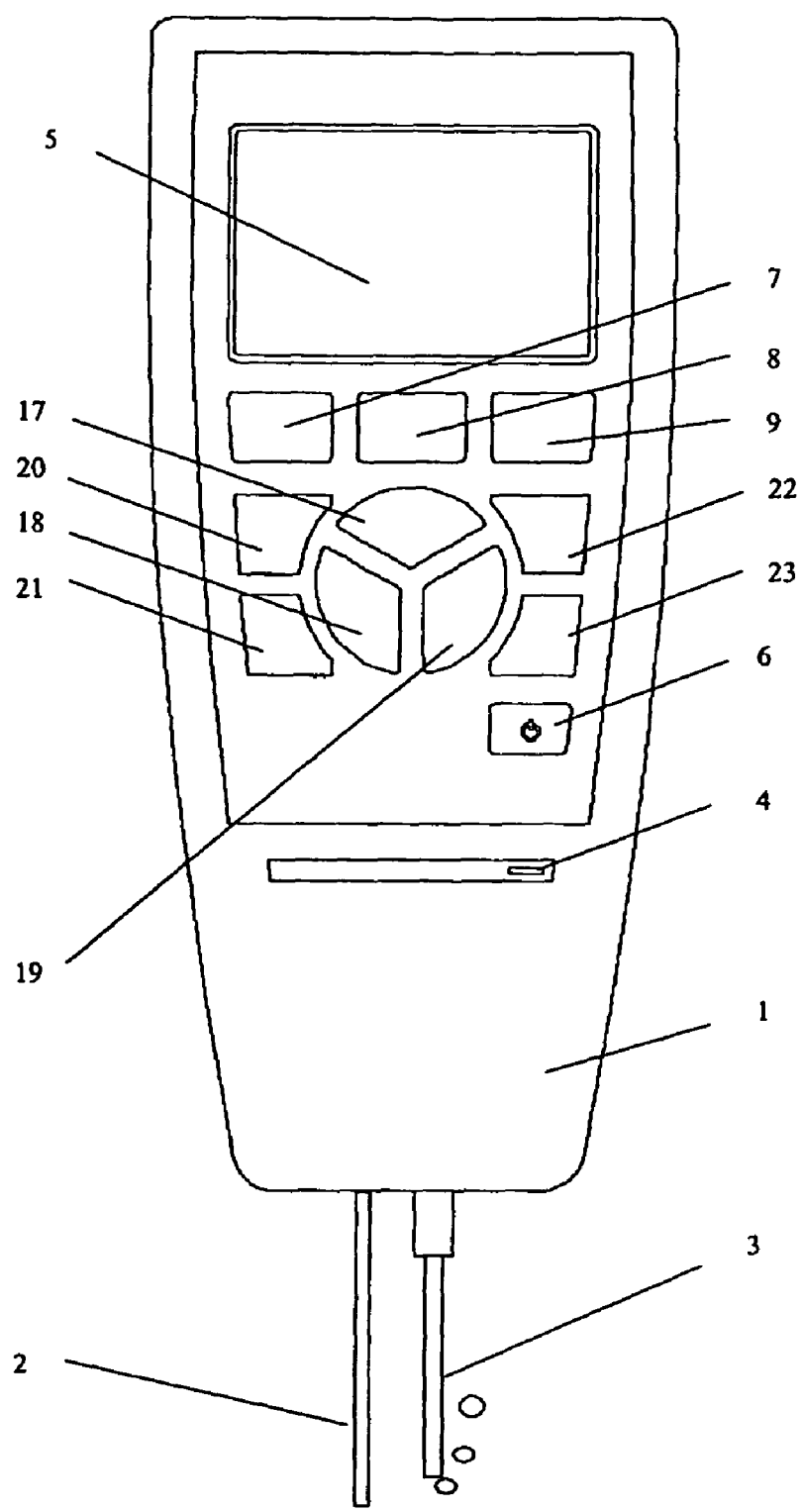

10 Claims, 2 Drawing Sheets ated current of the integrated air pump, to generate bubbles with different bubble life durations. The set bubble life duration or, respectively, bubble frequency is however not auto-
HANDHELD TENSIOMETER FEATURING AUTOMATIC REGULATION OF THE BUBBLE LIFE BY MEASURING AND REGULATING THE GAS VOLUME FLOW

CROSS-REFERENCE TO RELATED APPLICATIONS

This application is a National Phase of the PCT-application No.:
PCT/DE2007/000564
PCT Filing Date: Mar. 28, 2007

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND OF THE INVENTION

Field of the Invention

The invention relates to a hand tensiometer for measuring the surface tension of a liquid or of the substance concentration in a liquid according to a bubble pressure method.

The bubble life duration, which results at defined surface tension and dimensioning of the pneumatic system from the gas volume stream fed through the measurement capillary, is a significant parameter of the surface tension measurement value as it is the temperature of the sample. The concepts bubble life duration and surface age are employed synonymously in the practice and they define the time from the minimum to the maximum of the pressure in the bubble. The concept bubble frequency or, respectively, bubble rate indicates the number of bubbles exiting from the measurement capillary per time unit. The bubble frequency is employed in connection with bubble pressure tensiometers still only for reasons of compatibility or in connection with less precise measurements, since the reciprocal of the bubble frequency contained in addition to the bubble life duration the so-called dead time.

STATE OF THE ART

Description of Related Art Including Information Disclosed Under 37 CFR 1.97 and 1.98.

Hand tensiometers available commercially are equipped with a limited number of function defining components because of their construction size in comparison with stationary laboratories measurement apparatus.

A hand tensiometer is known from German printed patent document DE 20 2004 012 573 U1, which hand tensiometer consists of only a casing and which hand tensiometer is capable, with a manual setting possibility of the electric operating current of the integrated air pump, to generate bubbles with different bubble life durations. The set bubble life duration or, respectively, bubble frequency is however not automatically controlled by way of the hand tensiometer and varies therefore with time within a continuous measurement by drifting of the apparatus behavior, for example by warming up of the pump. A reliable reaching of a set point value of the bubble life duration and therewith a reachable measurement error of the value of the dynamic surface tension is of interest to the user.

The automatic control of the bubble life duration according to a set point value was realized (DE 20318463 U1) for the first time in a handheld bubble pressure tensiometer by way of automatically operating devices with a hand tensiometer of the applicant. This hand tensiometer for the measurement of the surface tension of liquids or the substance concentration in the liquid according to a bubble pressure method with automatically controlled bubble life duration exhibits a casing with at least one measurement capillary attached thereto as well as possibly further sensors and contains operating and display means, a current supply, a gas source for the generation of bubbles at least one measurement capillary, means for setting off bubble life durations (bubble frequency), as well as an electronic/processor unit for the control of all internal processes and the storage of data, wherein means for automatic control of the bubble life duration or, respectively, bubble frequency or a succession of changeable bubble rates according to one or several set point values are furnished. The bubble pressure is measured and the gas volume stream for generating the bubbles is not measured. The same holds for a hand measuring apparatus according to German printed patent document DE 20 310 173 U1.

Furthermore, a hand tensiometer operating according to a bubble pressure method for measuring the surface tension of liquids is described in the German Patent DE 19636644 C1, which hand tensiometer on the one hand exhibits a casing with at least one therein attached measurement capillary as well as possibly further sensors to as well as operating agents and display means, a current supply, a gas source for the generation of bubbles at the measurement capillary, means for controlling the gas volume stream entered into the measurement capillary for the generation of the exit of bubbles with a fixed selectable frequency or with automatic frequency sweep, as well as an electronic/processor unit for the control of all internal processes and storage of data and which hand tensiometer on the other hand stores measurement results such as bubble frequency, temperature and so on together with date/time, thus exhibits a data storage and is operable in various operational modes amongst which are two measurement modes. Here again the gas volume stream is not measured, but the bubble pressure is measured.

Critique of the State-of-the-art

The recited hand tensiometers are still subject to improvement as well as are additionally known hand tensiometers.

In this direction the automatic control of the hand tensiometers according to German printed Patent document DE 20318463 U1 operates sufficiently rapid within certain limits, because only after each finished bubble detection there is present an input value for the automatic control and because the device components for the volume stream generation are subject to a certain drifting and have to be adjusted or because the surface tension of the sample is changeable. Therefore a longer time is necessary to automatically control bubble life durations of more than one second or even several set point values of the bubble life duration or the defined sequence of different bubble life durations.

The operation of miniaturerized hand tensiometers is realized with only a few keys in view of a lack of sufficient suitable outer surface. The calling in of measurement functions is therefore realized by way of menu planes, which renders the operation awkward for persons without training. Several predefined measurement modes for performance exclusively by way of a hand tensiometer are not known.

Measurement values are usually stored in a memory storage in hand tensiometers, wherein the memory storage allows an identification of the measurement only by way of the date or of the memory place number. The access to a memory storage organized in this way is awkward and leads to confusion and errors.

Hand tensiometers furnish data through a PC interface. The direct communication with external periphery such as metering devices or with a PLC "programmable logic controller" is not possible.

Changes of the measurement track, such as for example the behavior of the measurement capillary lead to a maladjusting of the hand tensiometer. The behavior of a hand tensiometer can be determined, when a measurement is performed in a liquid with known surface tension. These measurement values can equally be employed for a calibration. However, an adjustment is not indicated or desired in each case. If therefore an adjustment is to be performed only if needed, then consequently two measurements have to be performed, the first one for determining the measurement behavior ("calibration") and the second for the proper adjustment. The corresponding time will be required for two such processes.

Further disadvantages of handling can be seen in a cable bound communication.

If several samples are measured or for example in production plants with several cleaning baths, several measurement points are sought out and the obtained measurement values are placed in the apparatus storage, it is possible that despite the sorting according to the kind of the measurement nevertheless an interchange of the samples occurs.

BRIEF SUMMARY OF THE INVENTION

Purposes of the Invention

It is an object of the Invention to develop a hand guided bubble pressure tensiometer, which, starting from the hand tensiometer according to German printed Patent document DE 20318463 U1, which avoids the recited disadvantages substantially. In particular a quicker automatic control of the bubble life duration is to be performed according to a set point value and an improved operation and readability also contribute to the rapidity of a measurement and to improved use of the measurement data as does the confusion free access to internal storage contents, a direct communication with external periphery, such as metering devices or a PLC "Programmable Logic Controller", and an only calibration if needed.

Resolution of the Object

The object is resolved according to the present invention by way of the features of the claim 1, wherein additional advantageous embodiments of the Invention with respect to improved properties of a hand tensiometer are given in the dependent claims. The independent claim 12 further gives a method for measuring a surface tension or of a material concentration with a hand tensiometer.

Embodiment

The Invention including its advantages is to be described in more detail by way of an embodiment example.

BRIEF DESCRIPTION OF THE SEVERAL VIEWS OF THE DRAWING(S)

There is shown in:
FIG. 1 the operating side of a hand tensiometer for measuring the surface tension or substance concentrations,
FIG. 2 a block circuit diagram of the pneumatic system for measuring the volume stream, and
FIG. 3 pressure signals depending on the forming bubble at the capillary of a bubble pressure tensiometer.

DETAILED DESCRIPTION OF THE INVENTION

The operation of a completely independently usable hand tensiometer is easy to survey for the user and is arranged without complicated menus, whereby the measurement duration can be reduced substantially. It is furnished for this purpose to call different predefined measurement courses by way of direct access keys. It is particularly advantageous for various tasks presented for example to measure only one measurement value for this surface tension of a measurement liquid or substance concentration in a liquid, for which purpose a measurement mode "individual measurement value" can be called up with a correspondingly characterized key 17. This mode allows a particular simple comparison of the measurement value with a set point value, possibly with automatic output of the deviation. A measurement mode "online" can be called the same way for a continuous measurement at a certain bubble life duration with a further key 19 and a measurement mode "auto" can be called with a third key 18 for measurement in case of a succession of different bubble life durations.

Sequences of the various support position density of the bubble life durations to be set in the hand tensiometer are predefined furthermore for simplified handling for the latter recited measurement mode "auto" and can be selected. For example, 10 measurement values are coordinated to the preset ["low"] and 50 measurement values are coordinated to a further preset ["high"], in each case with different bubble life durations.

In order to enable a measurement of the sample temperature already prior to the start of a surface tension measurement without cumbersome starting from the same as well as of each arbitrary state of the hand tensiometer, an additional direct selection key 20 ["temperature"] is furnished for a quick determination of the temperature measurement value, which is received by the temperature sensor 2 attached to the casing 1 of the hand tensiometer.

The cleaning procedure of a measurement capillary 3 exchangeably attached at the casing 1 is to started under increased volume stream with a further key 21 ["cleaning"] under key depression.

The use of an additional optical signal device, for example of a bright LED-lamp 4 or of a conventional illuminating agent, allows to call attention effectively and quickly with regard to operating states of the hand tensiometer.

According to a further embodiment of the hand tensiometer, a rear illuminating display 5 is furnished for example by way of very flat and current saving EL-foils.

In order to form the measurement data storage easy to survey and useful, the measurement data storage advantageously and fitting to the various kinds of measurement is subdivided in at least two regions. A region "individual measurement value" can serve for storing measurements with only a measurement value, a region "online" can serve for storing of measurement values with constant automatic control bubble life duration as well as a region "auto" can serve for storing of measurements with successions of different bubble life durations or bubble frequencies. Both for the storing as well as for the reading out, the regional access to the memory storage is then possible.

The hand tensiometer is additionally to the PC interface or also without PC interface with one or several unidirectional or bidirectional process interfaces to peripheral apparatus furnished for the direct communication of the hand tensiometer with external periphery such as metering devices, a PLC "Programmable Logic Controller" or with a protocol printer, which peripheral apparatus is suitable also without the PC to be controlled exclusively with the hand tensiometer, for example by switching outputs, current interfaces, RS232, Profibus or the like not illustrated here in detail. It is particularly advantageous when the interfaces are performed wireless. Furthermore the interfaces can be equipped such that the hand tensiometer can be operated remotely, for example by way of simple contacts for example for starting of individual measurement modes. It is therewith possible to automate in a simple way for example cleaning plants or test equipment in the laboratory with hand tensiometers without that the user has to integrate the PC into his or her process control.

The adjustment of the hand tensiometer is performed by way of a single measurement of a liquid with known surface tension such that initially only the calibration data are determined and qualitatively put out, for example "adjustment not required", "adjustment required" or quantitatively put out, for example "2% deviation", "0.5 mN/m deviation". The key 21 ["cleaning"] serves again to start the calibration which key 21 is actuated a second time for this purpose. Thereupon the calibration data can be considered by the user and by selection either be employed for the new adjustment of the hand tensiometer or can be thrown out, whereby the previous adjustment remains active. The manual selection of the use or of the throwing out of the calibration data can of course also be performed automatically through the hand tensiometer according to predefined rules.

A measurement can be stored with the key 23 ["storing"] upon key depression and the storage contents of the data storage can be read out with the key 22 ["read out"] upon key depression.

In addition the hand tensiometer comprises an on/off key 6 and three keys 7, 8, 9 disposed below the display 5, wherein the function of these keys is predetermined by associated software.

In order to attach the hand tensiometer for longer measurements securely to a stand and in order not to have to hold the hand tensiometer in the hand thereby consuming time, a partially enveloping shell not illustrated in detail is adjustably connected to the stand, wherein the hand tensiometer can be inserted into the shell from above in the neighborhood of the center of gravity or reaching the center of gravity and the hand tensiometer is held in measurement position. This shell can be furnished with contacts, wherein the contacts produce the connection of the hand tensiometer with interface or network adapter cables simply by plugging in of the hand tensiometer into the holder.

Figure 2:
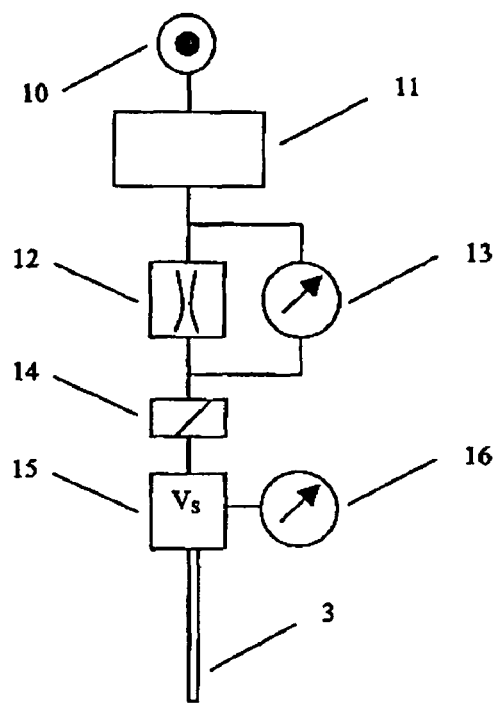

The automatic control of the bubble life duration or a succession of these according to one or several pre-given or fixedly installed set point value(s) by measuring and setting a gas volume stream is to be illustrated in more detail by way of FIG. 2.

The pneumatic system comprises a gas source 10, for example a pneumatic pump, a buffer storage 11, which generates constant gas pressure situations, a volume stream flow through meter, for example comprising the difference pressure meter 13 disposed parallel to a pneumatic resistance 12, a valve 14, wherein the valve 14 is internally set by the hand tensiometer and a system volume arrangement out of a system volume chamber 15, wherein the pressure sensor or difference pressure sensor 16 for measuring of the bubble pressure is connected to the system volume chamber 15, and of the measurement capillary 3 connected to the system volume chamber 15.

It is furnished according to the present Invention to obtain a steady guide value for the automatic control of the bubble life duration independent for example of the pressure of the gas source 10, of the actual setting of the valve 14, or of the surface tension of the liquid for accelerating the automatic control of the bubble life duration.

A certain gas volume stream has to be fed into the pneumatic system 15, 3 in order to generate a certain bubble life duration. If the required gas volume stream is present for at least one bubble life duration, then it is possible by feeding in of a gas volume stream inversely proportional to the bubble life duration to set sufficiently precise with a few bubbles and therewith quickly to set. For this purpose the gas volume stream through the valve 14 has to be constantly readjusted because of the changeable measurement conditions.

The hand tensiometer according to the present Invention comprises therefore a sensor 13 in the casing 1 for measuring the volume stream (for example in the kind of a difference pressure sensor 13 of a pneumatic resistance 12 or performed as the commercially available stream sensor without pneumatic resistance, as well as means for automatically controlling this volume stream to the in advance calculated value for example in the form of the software directed adjusted valve 14, wherein the pre-calculated value correlates with the automatically controllable set point bubble life duration. An automatically controllable pump or a pulsed switching valve with following smoothing of the gas volume stream are acting in the same direction.

It is use full to store the designation together with the data set during the depositing in the storage, which characterizes the sample or the measurement location of this sample (for example bath1, bath2 . . . ) in order to avoid confusion between several measurement values. Based on this information the desired data set can be found quicker and more safely. This input is simplified, if the identity is entered automatically with a transponder or bar code reader.

Figure 3:
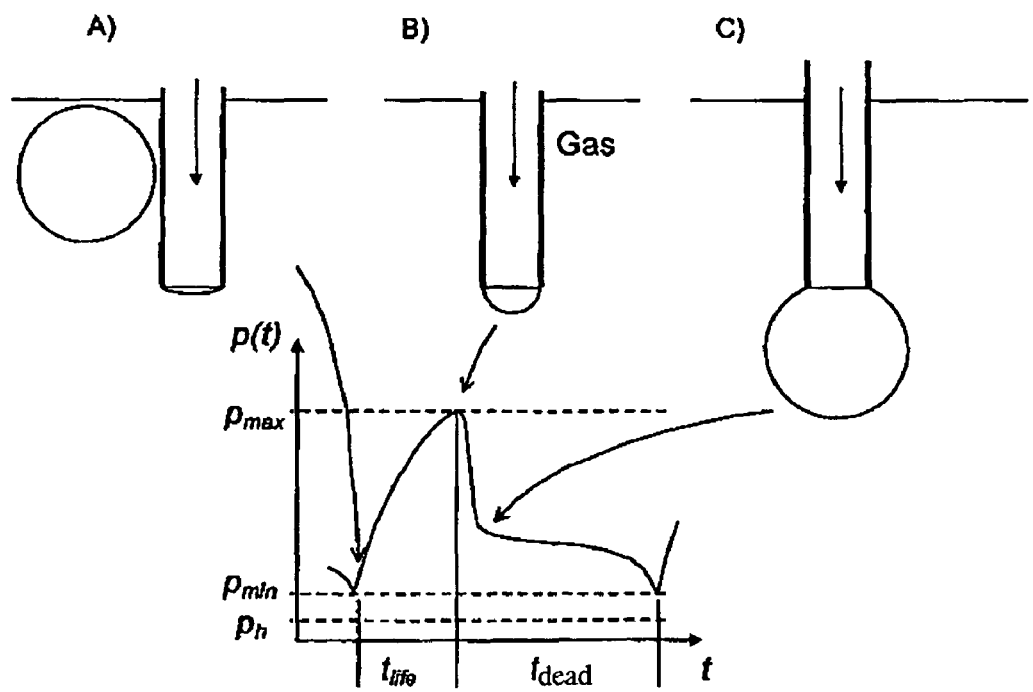

The pressure signal with the bubble pressure method is shown in FIG. 3 with the values maximum pressure $p_{max}$, minimum pressure $p_{min}$, hydro steady pressure $p_h$, bubble life duration (=surface age) $t_{life}$, and dead time $t_{dead}$. State A) shows the formation of a new bubble after the ripping off of a preceding bubble, state B) shows a bubble formed as a half sphere and state C) shows a sphere shaped blown up bubble shortly before the ripping off of the bubble. It can be recognized that with a bulging out of the bubble at the measurement capillary up to a half sphere the pressure in the bubble and therewith in the measurement system rises to a maximum value $p_{max}$ and following with continuing bulging out to the ripping off of the bubble from the capillary sinks again to a pressure minimum $p_{min}$. The covering with tensides occurring in the time $t_{life}$ up to reaching the pressure maximum $p_{max}$ determines the value of the pressure maximum $p_{max}$, correlating with the dynamic surface tension. The remaining time of a bubble formation cycle is the dead time $t_{dead}$.

The invention claimed is:

1. A hand tensiometer for measuring the surface tension of liquids or for measuring of substance concentrations in a liquid wherein a gas volume stream entered from a pump (10) through a buffer storage (11) into a measuring capillary (3) forms bubbles in the liquid at the end of the measuring capillary (3), and wherein means for steady measuring of the gas volume stream and a valve (14) internally set by the hand tensiometer is furnished for adjusting the gas volume stream and therewith for setting the bubble life duration.

2. The hand tensiometer according to claim 1 characterized in that the means for measuring of the gas volume stream is a difference pressure meter impacted over a pneumatic resistance (12).

3. A hand tensiometer for measuring the surface tension of liquids or for measuring the substance concentrations in a liquid comprising
- a pump (10) for furnishing a gas volume stream;
- a buffer storage (11) connected to the pump (10) and receiving the gas volume stream from the pump (10);
- a measuring capillary (3) connected to the buffer storage (11) for transferring the gas volume stream from the buffer storage (11) into the measuring capillary (3);
- a liquid receiving an end of the measuring capillary (3) for forming bubbles in the liquid at the end of the measuring capillary (3);
- means (13) connected to the buffer storage (11) for steady measuring of the gas volume stream; and
- a valve (14) internally set by the hand tensiometer is furnished for adjusting the gas volume stream and therewith for setting the bubble life duration.

4. The hand tensiometer according to claim 3, further comprising
- a pneumatic resistance (12) connected to the buffer storage (11), wherein the difference pressure meter (13) is disposed parallel to the pneumatic resistance (12).

5. A hand tensiometer for measuring the surface tension of liquids or for measuring of substance concentrations in a liquid comprising
- a pump (10) for furnishing a gas volume stream;
- a buffer storage (11) connected to the pump (10) and receiving the gas volume stream from the pump (10);
- a pneumatic resistance (12) connected to the buffer storage (11);
- a difference pressure meter (13) for steady measuring of the gas volume stream and connected to the buffer storage (11) and disposed parallel to the pneumatic resistance (12);
- a valve (14) connected to the pneumatic resistance (12) and to the difference pressure meter (13) and internally set by the hand tensiometer and furnished for adjusting the gas volume stream and therewith for setting the bubble life duration;
- a measuring capillary (3) connected to the valve (14) for transferring the gas volume stream from the valve (14) into the measuring capillary (3);
- a liquid receiving an end of the measuring capillary (3) for forming bubbles in the liquid at the end of the measuring capillary (3).

6. The hand tensiometer according to claim 5, wherein the pneumatic resistance (12) is connected to the buffer storage (11) and to the valve (14), wherein the difference pressure meter (13) is connected to the buffer storage (11) and to the valve (14) and disposed parallel to the pneumatic resistance (12).

7. The hand tensiometer according to claim 5, further comprising
- a system volume chamber (15) connected to the valve (14) and holding the measuring capillary (3);
- a pressure sensor or difference pressure sensor (16) is connected to the system volume chamber (15) for measuring of the bubble pressure.

8. The hand tensiometer according to claim 5, wherein the buffer storage (11) generates a constant gas pressure.

9. The hand tensiometer according to claim 5, wherein the gas volume stream through the valve (14) is constantly readjusted because of changeable measurement conditions.

10. The hand tensiometer according to claim 5 further comprising a casing (1), wherein the difference pressure meter (13) for steady measuring the gas volume stream is disposed in the casing (1), wherein the adjusted valve (14) is software directed, and wherein a pre-calculated value correlates with the automatically controllable set point bubble life duration.

\* \* \* \* \*